United States Patent [19]

Edwards et al.

[11] Patent Number: 5,275,162
[45] Date of Patent: Jan. 4, 1994

[54] VALVE MAPPING CATHETER

[75] Inventors: Stuart D. Edwards, Los Altos; Russell B. Thompson, San Leandro; Rand T. Pugmire, Mountain View, all of Calif.

[73] Assignee: EP Technologies, Inc., Sunnyvale, Calif.

[21] Appl. No.: 982,233

[22] Filed: Nov. 25, 1992

Related U.S. Application Data

[63] Continuation of Ser. No. 790,393, Nov. 8, 1991, abandoned.

[51] Int. Cl.⁵ .............................................. A61B 5/042
[52] U.S. Cl. ..................................... 128/642; 607/122
[58] Field of Search ............... 128/642, 784, 786, 804; 606/41, 34

[56] References Cited

U.S. PATENT DOCUMENTS

| | | | |
|---|---|---|---|
| 4,355,646 | 10/1982 | Kallok et al. | 128/786 |
| 4,444,195 | 4/1984 | Gold | 128/786 |
| 4,892,102 | 1/1990 | Astrinsky | 128/419 PG X |
| 4,896,671 | 1/1990 | Cunningham et al. | 128/642 |

FOREIGN PATENT DOCUMENTS

| | | | |
|---|---|---|---|
| 3017284 | 11/1981 | Fed. Rep. of Germany | 128/785 |
| 0249631 | 9/1987 | German Democratic Rep. | 128/642 |

Primary Examiner—Lee S. Cohen
Assistant Examiner—Brian L. Casler
Attorney, Agent, or Firm—Ryan, Kees & Hohenfeldt

[57] ABSTRACT

A method and apparatus for contacting heart valve tissue with a catheter tip electrode adapted for atrioventricular (AV) node mapping and modification is provided. The tip is conformed to rest stably and comfortably on a cardiac valve such as the mitral or tricuspid valve. The tip has a peanut shape consisting of two electrode lobes joined by a narrower connecting piece. The tip rests on the valve at the connecting piece and is secured by the adjoining lobes. The connecting piece itself may either be insulating or electrically conductive. The catheter may also include standard mapping and/or pacing electrodes. The catheter may further include a steering mechanism for positioning the catheter at various treatment sites in the heart.

7 Claims, 2 Drawing Sheets

VALVE MAPPING CATHETER

This is a continuation of copending application Ser. No. 07/790,393 filed on Nov. 8, 1991 abandoned.

TECHNICAL FIELD

This invention relates to a electro-physiological catheter tip for mapping and ablating arrhythmia-causing tissue by coupling radiofrequency energy to tissue surrounding the catheter tip. More particularly, this invention relates to a method and apparatus for contacting heart valve tissue with a catheter tip electrode adapted for atrioventricular (AV) node mapping and modification. The tip is conformed to rest stably and comfortably on a cardiac valve such as the mitral or tricuspid valve.

BACKGROUND OF THE INVENTION

The electrical charge of the outer membrane of an individual heart muscle cell is known as the "membrane potential". During each heartbeat, the membrane potential discharges (depolarizes) and then slowly recharges (repolarizes). The waveform of this periodic depolarization and repolarization is called the "transmembrane action potential." Mechanistically, the action potential is produced by a well-organized array of ionic currents across the cell membrane. These action potentials can be recorded, or mapped, using electrodes located at the distal end of a catheter inserted into a patient's heart.

At the turn of the century, it had also been recognized that a potential similar in shape to the later-discovered transmembrane potential could be recorded if one brought into contact a first electrode with an injured spot of the heart and a second reference electrode with an intact spot. Those signals became known as "injury potentials" or "monophasic action potentials" (MAPs) because of the waveform shape.

The further development of the science of MAPs may be found in U.S. Pat. No. 4,955,382, the disclosure of which is hereby incorporated by reference. It has been recognized that local heart muscle injury is not a prerequisite for the generation of MAPs, and that application of slight pressure with the tip against the inner wall of the heart will result in the generation of monophasic action potential signals. These signals can also be recorded reliably (i.e., without distortion) from a distal catheter tip electrode by using direct current (DC) coupled amplification.

This invention also relates to the thermal destruction, or ablation of endocardial tissue. Ablation of abnormal myocardial tissue (such as arrhythmia-causing tissue) is a therapeutic procedure used with increasing frequency for treatment of cardiac arrhythmias such as, for example, ventricular tachycardia. The medical technique of ablation is discussed in G. Fontaine et al., *Ablation in Cardiac Arrhythmias* (New York: Futura Publishing Co., 1987), and D. Newman et al., "Catheter Ablation of Cardiac Arrhythmias", in *Current Problems in Cardiology*, Year Book Medical Publishers, 1989.

Catheter ablation of ventricular tachycardia was first described in 1983 as a method for destroying arrhythmia-causing tissue. Typically, a pacing catheter is introduced into the left ventricle of the heart, and manipulated until the site of earliest activation during ventricular tachycardia is found, indicating the location of the problem tissue. Electrical energy, often high voltage DC pulses are then applied between a catheter-mounted electrode and an external chest wall electrode. In this way, arrhythmia-causing cardiac tissue is destroyed.

More recently, less drastic methods than high voltage pulses have been developed, which are painful (requiring general anaesthesia), and dangerous due to arcing and explosive gas formation at the catheter tip. The use of electromagnetic energy, more particularly radiofrequency (RF) or microwave energy, is currently in popular use. RF and microwave energy, unless otherwise noted, refers to energy in the electromagnetic spectrum from about 10 kHz to 100 GHz. RF ablation, usually in the range of 300–1200 kHz, is a safer alternative to high voltage DC pulsing in which RF energy is applied to the endocardium via an catheter electrode. Tissue destruction, or ablative injury, is effected by heating generated by the RF electric field. RF ablation results in a more controllable lesion size, with no gas or shock wave formation. Ablation may also be effected with energy having microwave frequencies, from about 700 MHz to 100 GHz. Ablation may be accomplished with a small ablating electrode located at the tip of a catheter inserted into a patient's heart.

Currently, no reliable method or apparatus exists to effectively, efficiently and evenly map or ablate the atrioventricular (AV) node. The AV node is the area separating the left atrium and left ventricle of the heart, which are connected by the mitral valve. Above the mitral valve lies the left atrial wall which is smooth and contiguous with the valve leaflet.

A traditional catheter tip electrode, which is cylindrical with a rounded tip, makes poor contact with both the valve tissue and the left atrial wall tissue situated directly above it. At the atrial wall, the tip slips and is unable to maintain continuous close contact with the tissue. At the valve itself, the constant opening and closing of the valve associated with the beating heart causes the tip to slip about the valve leaflet, rendering continuous close contact virtually impossible.

Important applications of the present invention are in the areas of studying and treating myocardial ischemia and cardiac arrhythmias. In particular, the present invention permits (1) precisely locating areas of myocardial ischemia, arrhythmia and tachycardia in the AV node area by using a catheter tip whose shape adapted to stably rest at the mitral valve; and (2) treating those ischemias, arrhythmias and tachycardias using a catheter tip whose shape is adapted to stably rest at the mitral valve.

SUMMARY OF THE INVENTION

The present invention overcomes the drawbacks of other catheter tips by permitting stable and accurate mapping and ablation of heart valve tissue through a catheter tip adapted to rest stably at the valve annulus. This catheter tip will generally have a "peanut" shape consisting of two electrode lobes joined by a narrower connecting piece. The tip rests on the valve at the connecting piece and is secured by the adjoining lobes. The connecting piece itself may either be insulating or electrically conductive.

The system of this invention may also include a steering mechanism for positioning the catheter in various locations in the heart. The mechanism permits the distal end of the catheter to be bent into varying shapes, and will include proximally located controls, a flexible steering shaft, and a distal apparatus for bending the distal end. Suitable steering mechanisms are disclosed in commonly-owned, copending U.S. application Ser. No. 07/473,667, the disclosure of which is hereby incorporated by reference.

Therefore, it is an object of the present invention to provide an apparatus for accurately mapping heart valve tissue.

It is another object of the present invention to provide an apparatus for accurately recording monophasic action potentials of heart valve tissue.

It is a further object of the present invention to provide an apparatus for accurately ablating heart valve tissue.

In accordance with the above objects, the present invention provides a catheter tip for mapping heart valve tissue. The tip comprises a rounded distal end electrode, a rounded proximal end electrode, and a connector connected to both the distal end and the proximal end, wherein the connector approximates a cylindrical shape and is narrower than the distal and proximal ends.

DETAILED DESCRIPTION OF THE INVENTION

Figure 1:
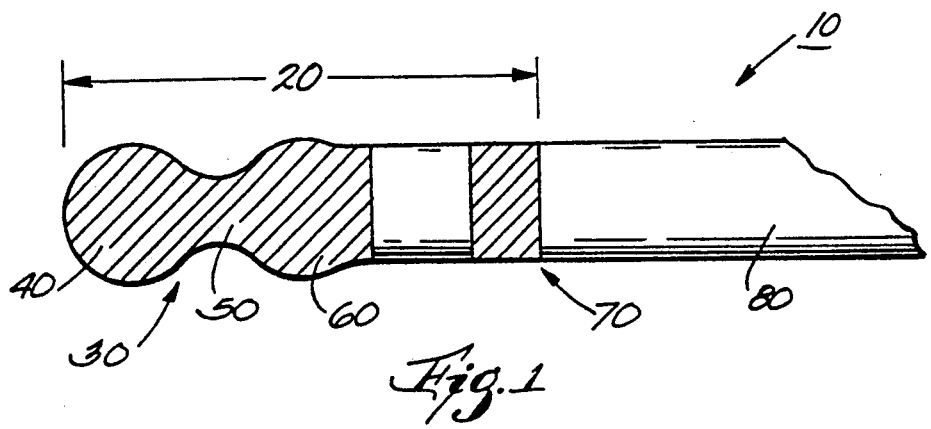
FIG. 1 is a schematic view of a catheter tip of the invention.

FIG. 1 shows the distal portion 20 of a probe catheter lo The distal portion comprises a catheter tip 30 and at least one ring electrode 70. Catheter tip 30 is a single electrode approximately 6 mm in length and 8 French cross-sectional diameter. Tip 30 has a double-lobed configuration, containing lobes 40 and 60 so that approximate spherical portions, and a narrower connecting portion 50 connecting the two lobes. Together, portions 40, 50 and 60 form a single electrode made of a conductive material such as platinum. The tip configuration is such that the tip may rest stably and comfortably on a heart valve such as the mitral valve. Located proximally to the catheter tip is ring electrode 70, which may be used for mapping or pacing purposes. The catheter may also contain additional ring electrodes located in a region 80 near the ring electrode shown in FIG. 1.

The tip electrode 30 may be used for mapping purposes, or may be used for recording MAP (monophasic action potential) signals as described in U.S. Pat. No. 4,955,382, or may be used to ablate tissue with radiofrequency energy, as described in U.S. Pat. No. 4,945,912.

Figure 2:
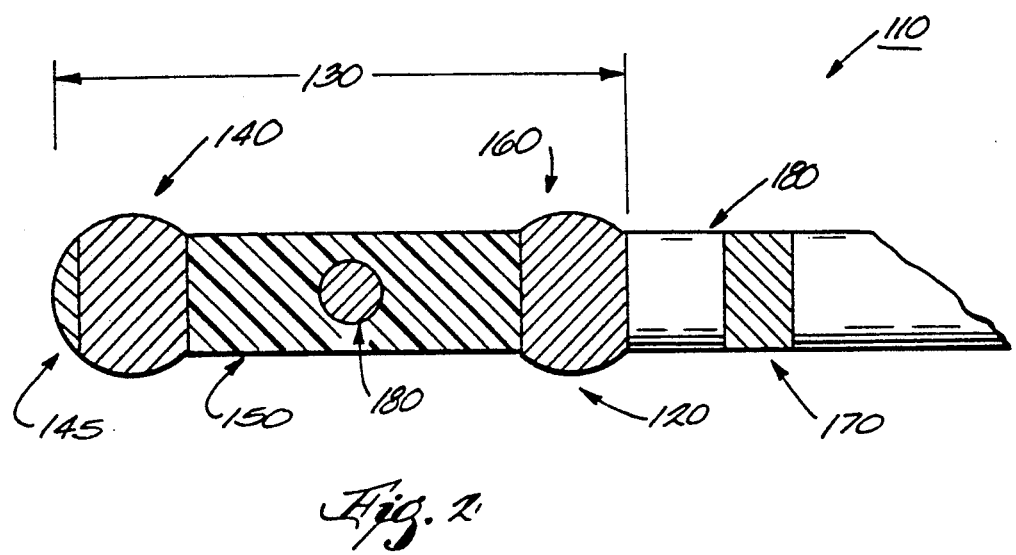
FIG. 2 is a schematic view of an alternate embodiment of the catheter tip of the invention.

FIG. 2 shows an alternate embodiment of the catheter tip of this invention. FIG. 2 shows the distal portion 120 of a catheter probe 110. The distal portion comprises a catheter tip 130 and at least one ring electrode 170. Catheter tip 130 is from 4 to 8 mm in length. Tip 130 is of a double-lobed configuration in the same manner as tip 30 in FIG. 1, but includes two separate electrodes—distal electrode 140 and proximal electrode 160—which are approximately spherical with an 8 French diameter. The spherical electrodes 140 and 160 are connected by a narrower nonconductive connecting portion 150. Preferably, connecting portion 150 is a non-conductive sleeve having a central bore for housing electrical and/or steering wires, made of a material such as polysulfone.

Located at the distal tip of the distal spherical electrode 140 is a separate electrode 145 for recording MAP potentials. Electrode 145 is a sintered depolarizing electrode, preferably formed of silver-silver chloride. Located proximally from electrode 145 and within the non-conductive connecting portion 150, is side dot electrode 180, which serves as the "indifferent" electrode for tip electrode 145. Side electrode 180 is electrically insulated from the tip electrode by the insulating connecting portion 150. Together, these two electrodes record the MAP signals.

Tip portion 130 has a configuration that permits it to rest stably and comfortably on a heart valve such as the mitral valve. Located proximally to the catheter tip is ring electrode 170, which may be used for mapping or pacing purposes. The catheter may also contain additional ring electrodes located in a region 180 near the ring electrode shown in FIG. 2.

The tip configuration 130 is used for mapping purposes, or may be used for recording MAP (monophasic action potential) signals as described in U.S. Pat. No. 4,955,382. It may also be used to ablate tissue with radiofrequency energy, as described in U.S. Pat. No. 4,945,912.

Figure 3:
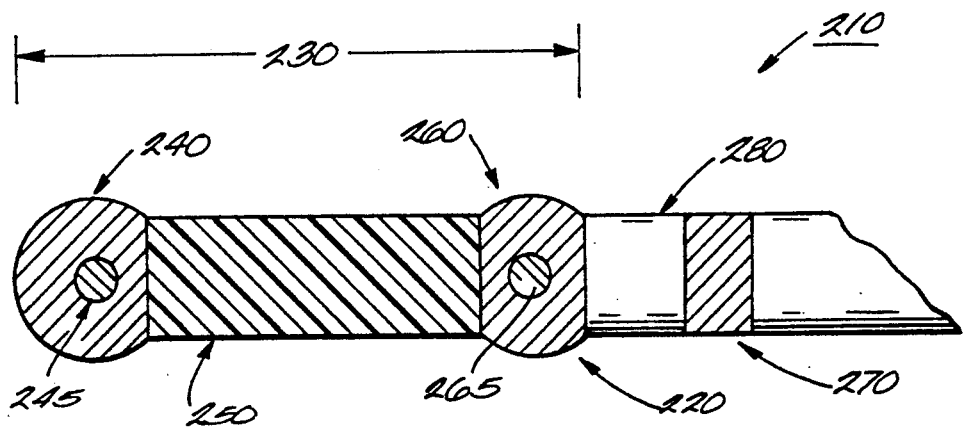
FIG. 3 is a schematic view of another alternate embodiment of the catheter tip of the invention.

FIG. 3 shows yet another alternate embodiment of the catheter tip of this invention. FIG. 3 shows the distal portion 220 of a catheter probe 210. The distal portion comprises a catheter tip 230 and at least one ring electrode 270. Catheter tip 230 is from 4 to 8 mm in length. Tip 230 is of a double-lobed configuration similar to that shown in FIG. 2, including the two approximately spherical electrodes 240 and 260 and the narrower nonconductive connecting portion 250.

The tip shown in FIG. 3 also contains thermistor thermocouples 245 and 265 located on the surface of the distal and proximal spherical electrodes. These thermistors are inserted onto the electrode surfaces and are electrically attached to wires that extend to the proximal end of the probe to convey thermal information from the tip to the end user. The structure and use of these thermistors are further described in commonly-owned copending U.S. Application entitled "Electrode and Associated Systems Using Thermally Insulated Temperature Sensing Element", U.S. No. 790,578, filed on even date herewith.

Tip portion 230 has a configuration that permits it to rest stably and comfortably on a heart valve such as the mitral valve. Located proximally to the catheter tip is ring electrode 270, which may be used for mapping or pacing purposes. The catheter may also contain additional ring electrodes located in a region 280 near the ring electrode shown in FIG. 3.

Figure 4:
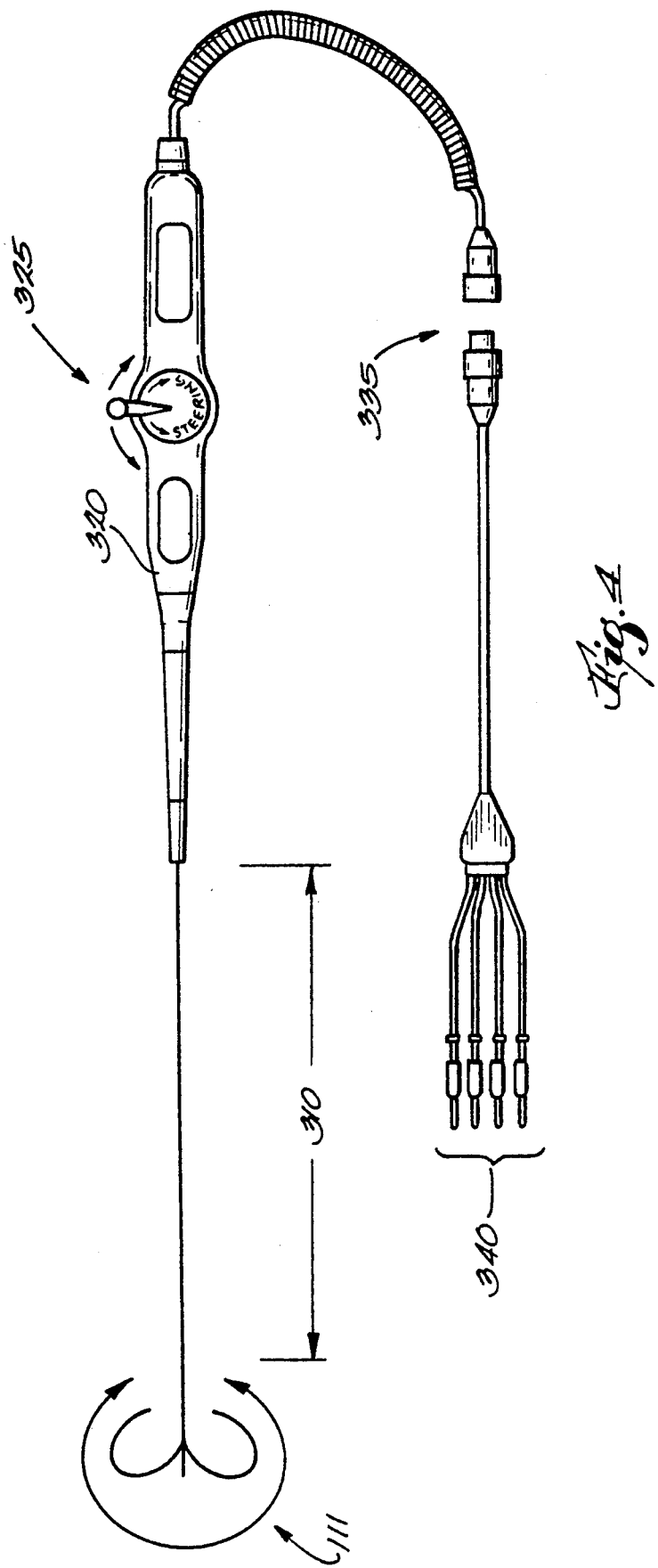
FIG. 4 is a schematic view of an overall catheter system in which the catheter tips of this invention may be used.

FIG. 4 shows a typical catheter system 300 in which the catheter tips of this invention may be used. Tip 111 may be a catheter tip as shown in any of FIGS. 1–3. The range of motion of tip 111, controlled by the steering mechanism, is also depicted in FIG. 4. The electrodes and thermistors in the tip are electrically connected by wires running through the distal end of tube 310, through handle 320, and ultimately to leads 340 to appropriate power sources and meters at the proximal end of the system. Tube 310 may also house wires that comprise part of the steering mechanism of the system (not shown). Tube 310 is connected at its proximal end to handle 320 which is used by the physician to maneuver the catheter system and position the catheter probe tip properly in the patient. Handle 320 contains steering lever 325 to operate the steering mechanism. Wire leads 340 are optionally connected to the wires in handle 320 through a connector 335.

It will be understood that contained within tube 310 in FIG. 4 are the necessary electrical leads to the electrodes contained in tip 111. The electrical lead to an ablating electrode may be connected to an electromagnetic energy source, such as a radiofrequency source or microwave source, for providing ablating energy to the catheter tip.

We claim:

1. A catheter tip for mapping heart valve tissue or for recording monophasic action potentials therein comprising:
    a distal end electrode, wherein a distal end thereof being rounded;
    a proximal end electrode of a rounded configuration; and
    a connector connecting the distal and proximal end electrodes, wherein the connector is an insulating material that approximates a cylindrical shape of reduced diameter with respect to the electrode and connecting the distal and proximal end electrodes and a thermistor located on a surface of at least one of said end electrodes.

2. The catheter tip of claim 1 wherein the insulating material is a polysulfone sleeve.

3. The catheter tip of claim 1 further comprising a thermistor located on the surface of the distal end electrode.

4. A catheter tip for ablating heart valve tissue comprising:
    a distal end electrode, wherein a distal end thereof being rounded;
    a proximal end electrode of a rounded configuration; and
    a connector connecting the distal and proximal end electrodes, wherein the connector is an insulating material that approximates a cylindrical shape of reduced diameter connecting the distal and proximal end electrodes and a thermistor located on a surface of at least one of said end electrodes and one of said end electrodes being an ablating electrode, and a lead means for connecting said ablating electrode to an electromagnetic energy source.

5. The catheter tip of claim 4 wherein the insulating material is a polysulfone sleeve.

6. The catheter tip of claim 4 further comprising a thermistor located on the surface of the distal end electrode.

7. The catheter tip of claim 4 further comprising a thermistor located on the surface of the proximal end electrode.

* * * * *